(12) United States Patent
Williams

(10) Patent No.: US 10,912,578 B2
(45) Date of Patent: Feb. 9, 2021

(54) CLAMPING DEVICE WITH PARALLEL JAW CLOSURE

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 205 days.

(21) Appl. No.: 16/261,702

(22) Filed: Jan. 30, 2019

(65) Prior Publication Data

US 2019/0321062 A1 Oct. 24, 2019

Related U.S. Application Data

(60) Provisional application No. 62/661,738, filed on Apr. 24, 2018.

(51) Int. Cl.
*A61B 17/29* (2006.01)
*A61B 17/00* (2006.01)
*A61B 17/072* (2006.01)

(52) U.S. Cl.
CPC .... *A61B 17/29* (2013.01); *A61B 2017/00022* (2013.01); *A61B 2017/07264* (2013.01); *A61B 2017/2924* (2013.01); *A61B 2017/2944* (2013.01)

(58) Field of Classification Search
CPC .......... A61B 17/29; A61B 2017/00022; A61B 2017/2944; A61B 2017/2924; A61B 2017/07264; A61B 17/122; A61B 2017/07214; A61B 2017/2936
See application file for complete search history.

(56) References Cited

U.S. PATENT DOCUMENTS

| | | | |
|---|---|---|---|
| 5,358,506 A | 10/1994 | Green et al. | |
| 6,662,690 B1 * | 12/2003 | Ploeger | B25B 7/12 81/318 |
| 6,716,232 B1 | 4/2004 | Vidal et al. | |
| 7,252,666 B2 | 8/2007 | Dycus | |
| 7,617,961 B2 | 11/2009 | Viola | |
| 8,403,197 B2 | 3/2013 | Vidal et al. | |
| 8,409,200 B2 * | 4/2013 | Holcomb | A61B 18/1445 606/51 |
| 8,616,427 B2 | 12/2013 | Viola | |
| 9,439,666 B2 * | 9/2016 | Kerr | A61B 17/29 |
| 10,568,626 B2 * | 2/2020 | Shelton, IV | A61B 90/03 |
| 2014/0336677 A1 | 11/2014 | Hessler | |
| 2018/0317914 A1 | 11/2018 | Badawi | |

* cited by examiner

*Primary Examiner* — Julian W Woo
(74) *Attorney, Agent, or Firm* — Carter, DeLuca & Farrell LLP

(57) ABSTRACT

A surgical clamping device includes a tool assembly having a first jaw and a second jaw. The first jaw includes a mount portion and a clamping portion and the second jaw includes a proximal portion having first and second side walls defining a central cavity. The mount portion of the first jaw is received within the central cavity of the second jaw. One of the mount portion of the first jaw or the proximal portion of the second jaw includes first and second cam members and the other of the mount portion of the first jaw or the proximal portion of the second jaw defines at least one cam slot that receives the first and second cam members. The at least one cam slot is configured to cause parallel closure of the first and second jaws.

18 Claims, 6 Drawing Sheets

CLAMPING DEVICE WITH PARALLEL JAW CLOSURE

CROSS-REFERENCE TO RELATED APPLICATION

This application claims the benefit of and priority to U.S. Provisional Patent Application No. 62/661,738 filed Apr. 24, 2018, the entire disclosure of which is incorporated by reference herein.

BACKGROUND

1. Technical Description

The present disclosure is directed to surgical clamping devices and, more particularly, to surgical clamping devices with parallel jaw closure for providing balanced tissue compression.

2. Background of Related Art

Surgical clamping devices for clamping tissue are well known in the art. These devices include vascular clamping devices which are used to occlude blood flow through vasculature. Typically, surgical clamping devices include a pair of jaws that are movable in relation to each other to clamp tissue positioned between the jaws. In some devices, the jaws are pivotally coupled to each other or to support structure at their proximal ends and are pivotal from an open position to a clamped position. In such embodiments, movement of the jaws from the open position to the clamped position tends to urge or extrude tissue from between the jaws during closure which results in uneven pressure distribution on the tissue.

In other known devices that clamp tissue between a pair of jaws such as surgical staplers, a mechanism is provided to effect parallel closure of the jaws to improve pressure distribution on tissue and to limit tissue extrusion from between the jaws during clamping of tissue. The mechanism may include spaced screws which support opposite ends of one or both of the jaw. The screws can be rotated to effect parallel closure of the jaws. Although these devices minimize tissue extrusion and provide a more uniform pressure distribution on tissue, the devices can be overly complex and provide limited access to the clamping surfaces of the jaws in the open position of the jaws.

Accordingly, a continuing need exists in the art for a tissue clamping device that is simple in construction yet provides the benefits of parallel closure.

SUMMARY

One aspect of the disclosure is directed to a surgical clamping device including a hand grip, an actuator assembly, an elongate body, and a tool assembly. The actuator assembly is supported on the hand grip. The elongate body defines a longitudinal axis and extends from the hand grip. The tool assembly is supported on the elongate body and includes a first jaw having a mount portion and a clamping portion, and a second jaw having a proximal portion. The proximal portion has first and second side walls that define a central cavity that receives the mount portion of the first jaw. One of the mount portion of the first jaw or the proximal portion of the second jaw includes first and second cam members and the other of the mount portion of the first jaw or the proximal portion of the second jaw defines at least one cam slot, wherein the first and second cam members are received in the at least one cam slot. The at least one cam slot is shaped to provide parallel closure of the first and second jaws and includes a distal portion defining an acute angle "ß" with the longitudinal axis and a proximal portion defining a second acute angle "Ω" with the longitudinal axis, wherein the angle "ß" is greater than the angle "Ω".

Another aspect of the present disclosure is directed to a tool assembly including a first jaw and a second jaw. The first jaw has a mount portion and a clamping portion, and the second jaw has a proximal portion. The proximal portion has first and second side walls that define a central cavity that receives the mount portion of the first jaw. One of the mount portion of the first jaw or the proximal portion of the second jaw includes first and second cam members and the other of the mount portion of the first jaw or the proximal portion of the second jaw defines at least one cam slot, wherein the first and second cam members are received in the at least one cam slot. The at least one cam slot is shaped to provide parallel closure of the first and second jaws and includes a distal portion defining an acute angle "ß" with a longitudinal axis of the tool assembly and a proximal portion defining a second acute angle "Ω" with the longitudinal axis of the tool assembly, wherein the angle "ß" is greater than the angle "Ω".

In embodiments, the mount portion of the first jaw includes the first and second cam members and the proximal portion of the second jaw defines the at least one cam slot.

In some embodiments, each of the first and second walls of the proximal portion of the second jaw defines a cam slot of the at least one cam slot.

In certain embodiments, the first and second cam members are longitudinally spaced from each other on the mount portion of the first jaw.

In embodiments, the first and second cam members extend radially outwardly from opposite sides of the mount portion of the first jaw.

In some embodiments, the mount portion of the first jaw defines the at least one cam slot.

In certain embodiments, the proximal portion of the second jaw supports the first and second cam members.

In embodiments, the first and second cam members extend between the first and second side walls of the proximal portion of the second jaw across the central cavity.

BRIEF DESCRIPTION OF THE DRAWINGS

Various embodiments of the presently disclosed clamping device are described herein below with reference to the drawings, wherein.

DETAILED DESCRIPTION OF EMBODIMENTS

Figure 1:
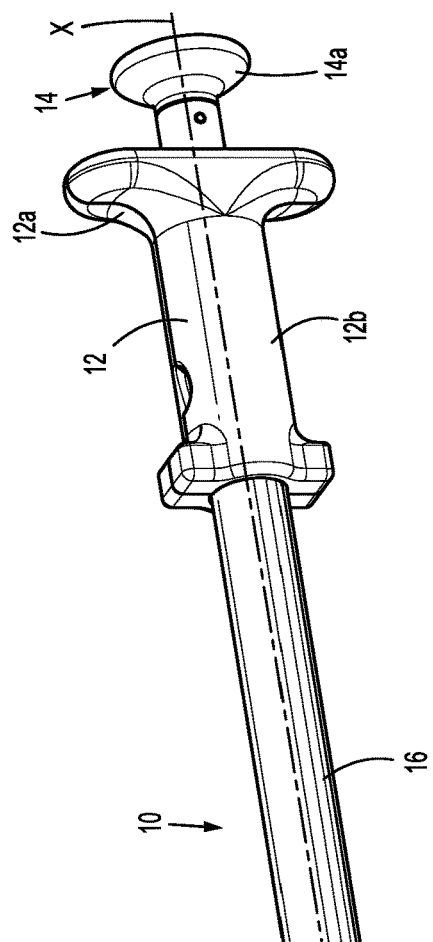
FIG. 1 is a side perspective view of an exemplary embodiment of the presently disclosed surgical clamping device with tool assembly in an open position.
Figure 1:
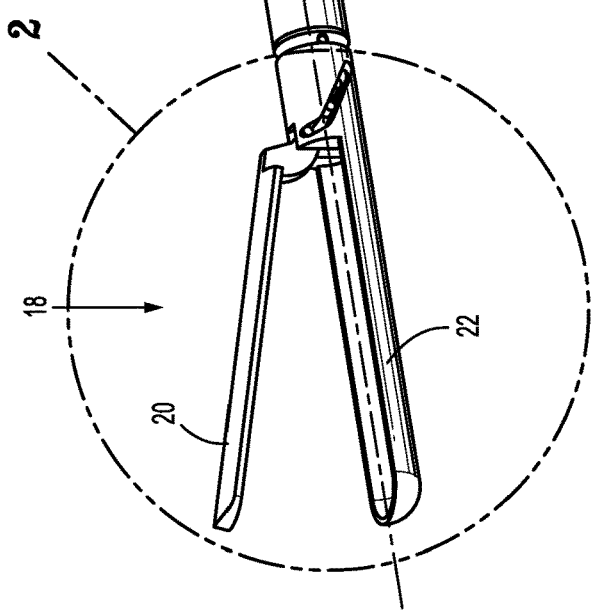

The presently disclosed clamping device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 2:
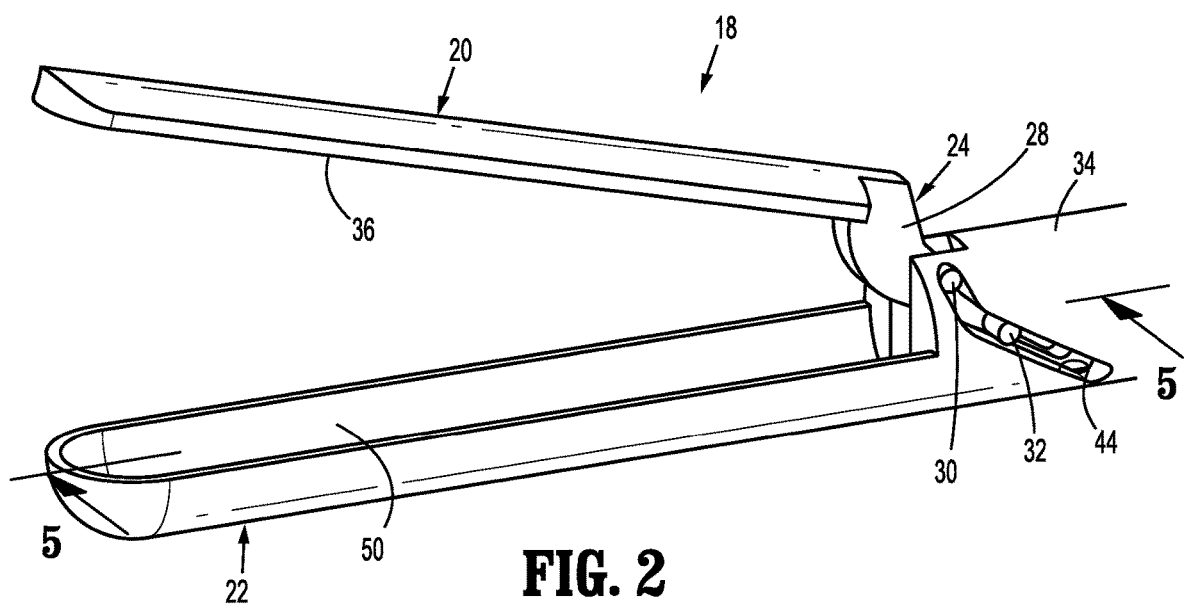
FIG. 2 is an enlarged view of the indicated area of detail shown in FIG. 1.
Figure 3:
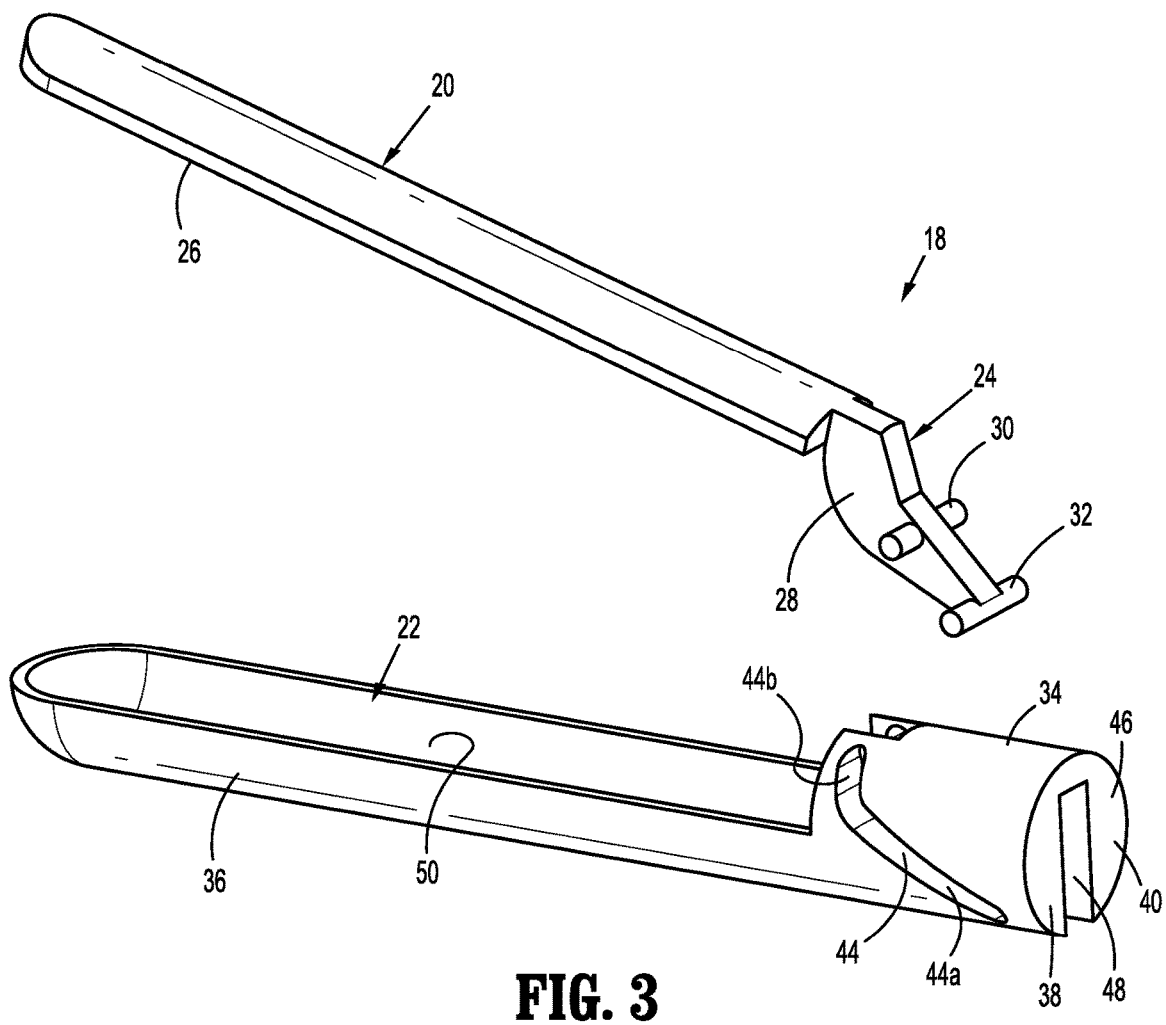
FIG. 3 is a side perspective view of the jaws of the tool assembly shown in FIG. 1 with parts separated.
Figure 7:
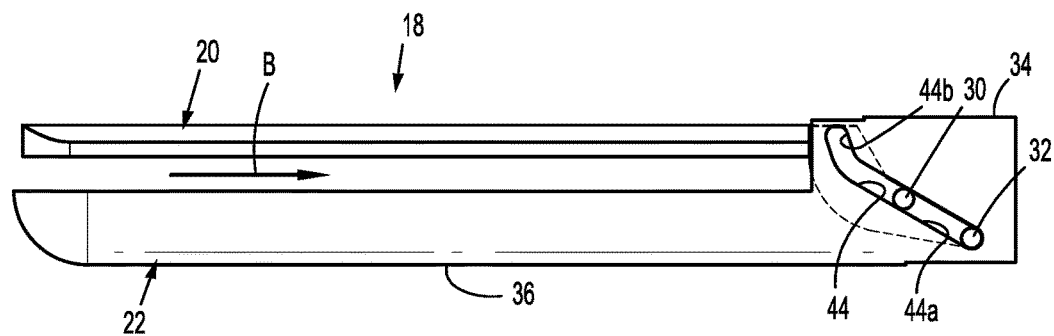
FIG. 7 is a side view of the tool assembly shown in FIG. 6 with the jaws in the clamped position.
Figure 8:
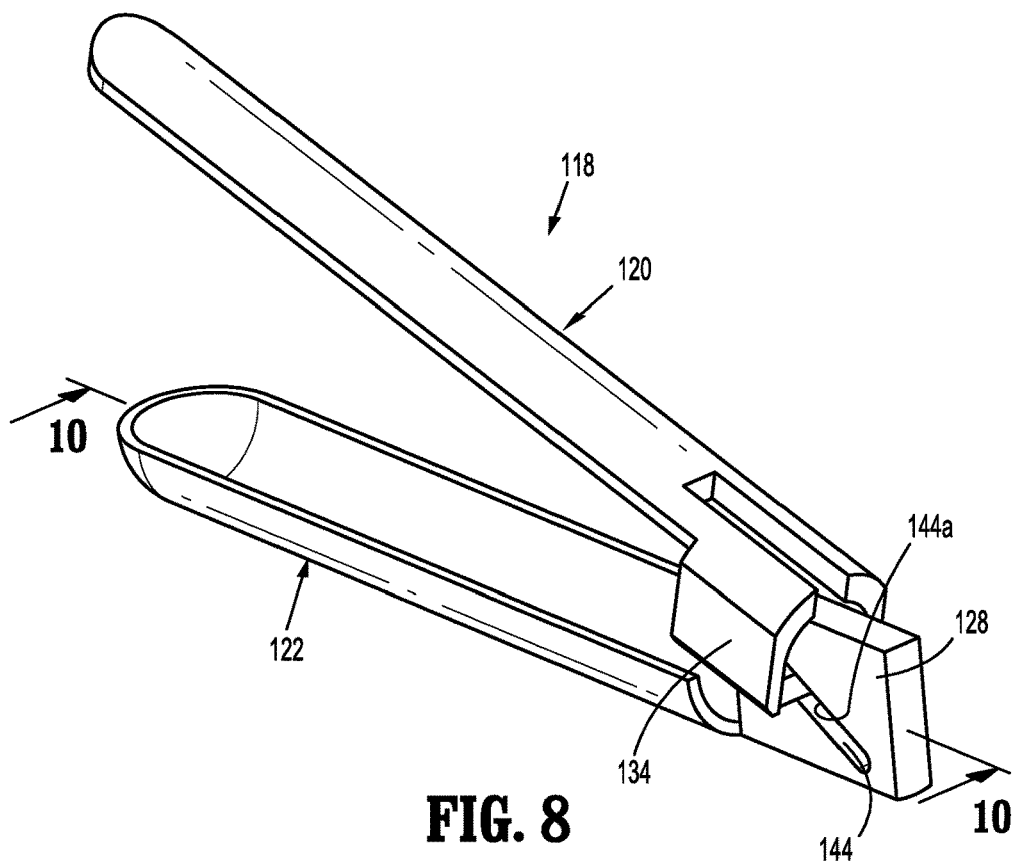
FIG. 8 is a side perspective view of an alternate embodiment of the tool assembly of the presently disclosed surgical clamping device with the tool assembly in an open position.
Figure 9:
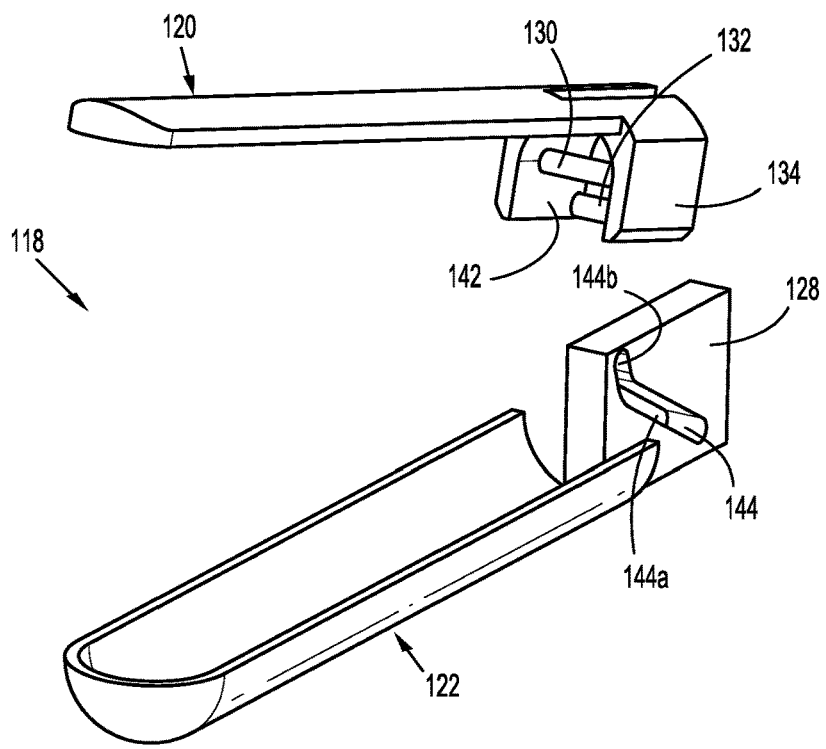
FIG. 9 is a side perspective view of the jaws of the tool assembly shown in FIG. 8 with parts separated.

Referring to FIG. 1, the presently disclosed surgical clamping device shown generally as 10 includes a hand grip 12, an actuator assembly 14, an elongate body 16 defining a longitudinal axis "X", and a tool assembly 18. In embodiments, the hand grip 12 is formed from molded half-sections 12a, 12b that are secured together using known fastening techniques including screws, welding, or the like. The actuator assembly 14 includes a knob 14a that is movable longitudinally in relation to the hand grip 12 to control operation of the tool assembly 18 as described in further detail below. The tool assembly 18 is supported on a distal portion of the elongate body 16 and includes a first jaw 20 that is supported in relation to a second jaw 22 for movement between an open position (FIG. 2) and a clamped position (FIG. 7). U.S. Provisional Application Ser. No. 62/581,064 ("the '064 Application") discloses a hand grip 12 and actuator assembly 14 suitable for use with the surgical clamping device described and is incorporated herein by reference in its entirety.

Referring to FIGS. 2-5, the first jaw 20 of the tool assembly 18 includes a mount portion 24 and a clamping portion 26. In embodiments, the mount portion 24 includes a central body portion 28 and first and second cam members 30, 32, respectively. The central body portion 28 of the mount portion 24 extends proximally from the clamping portion 26 and is received within a proximal portion 34 of the second jaw 22. The first and second cam members 30, 32 extend outwardly from each side of the central body portion 28 and are longitudinally spaced from each other. In embodiments, the first and second cam members 30, 32 are defined by a single cylindrical post that extends through openings in the central body portion 28. Alternately, the first cam member 30 can be formed by two separate posts supported on opposite sides of the central body portion 28 and the second cam member 32 can be formed by two separate posts supported on opposite sides of the central body portion 28.

In embodiments, the clamping portion 26 of the first jaw 26 includes a tissue clamping surface 36 that is movable from an open position (FIG. 2) in relation to the second jaw 22 to a clamped position (FIG. 7). Although not shown, it is envisioned that the first jaw 20 may be modified to perform a variety of different functions. For example, the first jaw 20 may be modified to form an anvil for receiving staples of a surgical stapling device. Alternately, the first jaw may be modified to receive a flow sensor for blood pressure measurement.

The second jaw 22 includes the proximal portion 34 and a distal portion 36 that extends distally from the proximal portion 34. The proximal portion 34 of the second jaw 22 defines first and second side walls 38, 40 that define a cavity 42 (FIG. 5) within the proximal portion 34 of the second jaw 22. Each of the side walls 38, 40 defines a cam slot 44 that receives one of the ends of each of the first and second cam members 30, 32. The cam slots 44 have a proximal portion 44a and a distal portion 44b. The distal portion 44b of the cam slots 44 defines an axis "Z" (FIG. 4) that defines an acute angle "ß" with the longitudinal axis "X" of the elongate body portion 16. The proximal portion 44a defines an axis "Y" (FIG. 4) that defines an acute angle "Ω" with the longitudinal axis "X" of the elongate body portion 16. The acute angle "ß" is greater than the acute angle "Ω". In embodiments, the proximal portion 34 of the second jaw 22 has a proximal wall 46 (FIG. 3) that defines a slot 48 that receives a distal end of the actuator assembly 14 (FIG. 1) as described in further detail below.

In embodiments, the proximal portion of the second jaw 22 is secured to a distal portion of the elongate body 16 such that the second jaw 22 is fixedly secured to the elongate body 16. As shown, the distal portion 36 of the second jaw 22 defines a concavity 50 that is positioned in juxtaposed alignment with the tissue clamping surface 36 of the first jaw 20 when the tool assembly 18 is in the clamped position (FIG. 7). In some embodiments, the concavity 50 is configured to receive an inflatable bladder (not shown) that in conjunction with sensors provided on the first jaw 20 is configured to facilitate internal blood pressure measurement such as described in detail in the "064 application. Although not shown, it is envisioned that the second jaw 22 may be modified to perform a variety of different functions. For example, the first jaw 20 may be modified to support a cartridge assembly for housing staples of a surgical stapling device.

Figure 5:
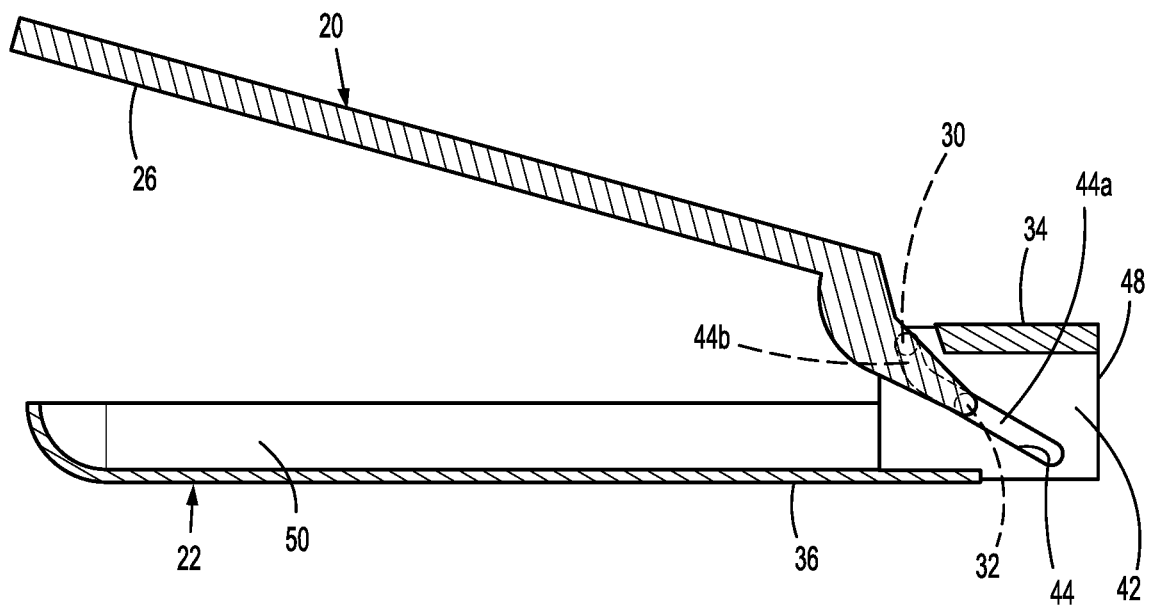
FIG. 5 is a cross-sectional view taken along section line 5-5 of FIG. 2.
Figure 5A:
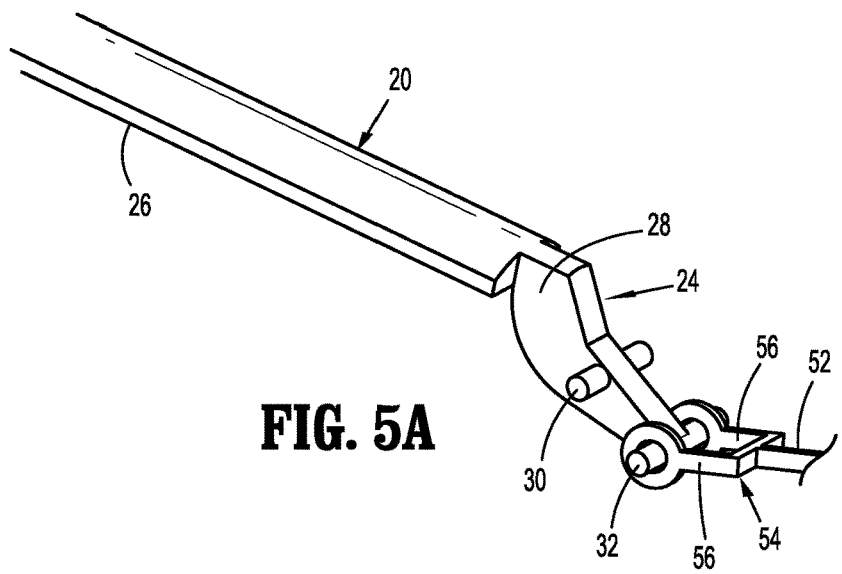
FIG. 5A is a side perspective view of a first jaw of the tool assembly and a distal end of an actuator assembly of the surgical clamping device shown in FIG. 1.

Referring to FIG. 5A, in embodiments, the actuator assembly 14 includes a distal link 52 that is rotatably coupled to the second cam member 32 such that the first jaw 20 can pivot in relation to the distal link 52 about an axis defined by the second cam member 32. In some embodiments, the distal link 52 defines a yoke 54 that has first and second spaced legs 56 supporting eyelets 58 that receive portions of the second cam member 32. The eyelets 58 receive the second cam member 32 to facilitate pivotal movement of the first jaw 20 in relation to the second jaw 22 and in relation to the distal link 52. The distal link of the actuator assembly 14 is longitudinally movable within the elongate body 18 (FIG. 1) to advance the first jaw 20 in relation to the second jaw 22 to move the tool assembly 18 between the open and clamped positions as described in detail below.

Figure 4:
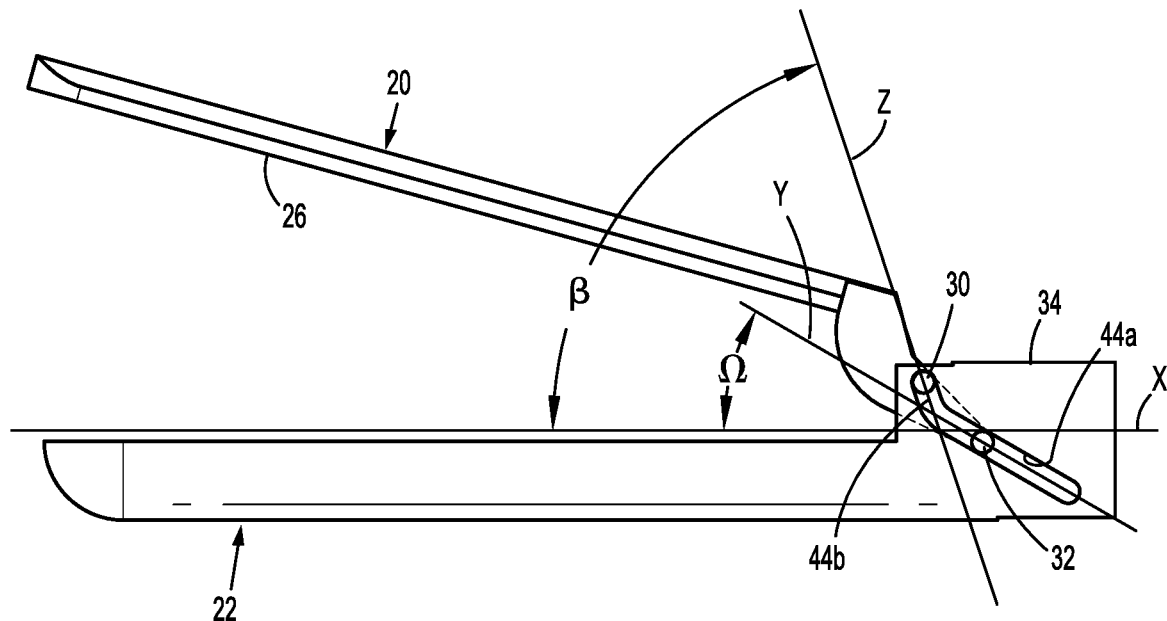
FIG. 4 is a side view of the tool assembly of the surgical clamping device shown in FIG. 1.

Referring to FIGS. 4 and 5, when the first jaw 20 is in its advanced position in relation to the second jaw 22, the first cam member 30 is positioned in the distal portion 44b of the cam slots 44 and the second cam member 32 is positioned in the proximal portion 44a of the cam slots 44. In this position, the first jaw 20 is angled upwardly from the second jaw 22 in the open position to facilitate placement of tissue between the first and second jaws 20, 22.

Figure 6:
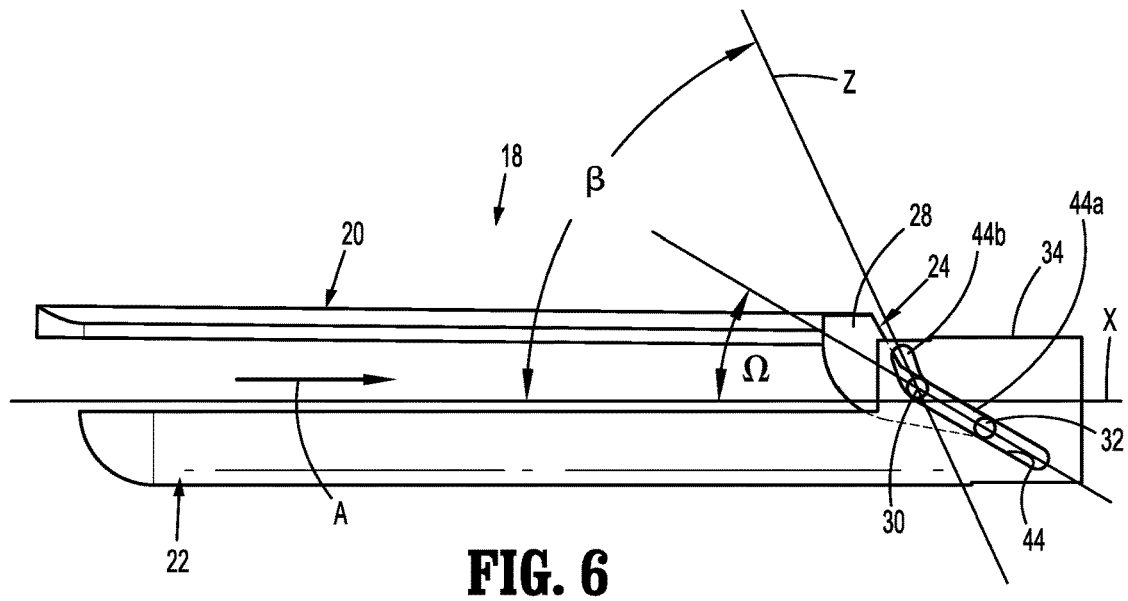
FIG. 6 is a side view of the tool assembly shown in FIG. 1 with the jaws in an intermediate position between the open position and a clamped position.

Referring to FIG. 6, when the actuator knob 14a (FIG. 1) of the actuator assembly 14 is retracted to move the first jaw 20 proximally in relation to the second jaw 22 in the direction indicated by arrow "A", the first and second cam members 30, 32 are moved proximally within the cam slots 44 of the second jaw 22 such that the first cam member 30 moves from the distal portion 44b of the cam slots 44 to the proximal portion 44a of the cam slots 44 and the cam member 32 moves along the proximal portion 44a of the cam slots 44. As the first cam member 30 moves through the distal portion 44b of the cam slots 44 at the angle "ß" and the second cam member 32 moves through the proximal portion 44a of the cam slots 44 at the angle "Ω", the first jaw 20 rotates in relation to the second jaw 22 from the open position (FIG. 4) to an intermediate position (FIG. 6). In the intermediate position, the first jaw 20 defines a longitudinal axis that is substantially parallel to a longitudinal axis of the second jaw 22.

Referring to FIG. 7, when the actuator knob 14a (FIG. 1) is retracted to move the first jaw 20 in relation to the second jaw 22 in the direction indicated by arrow "ß" to a fully retracted position, the first and second cam members 30, 32 move downwardly along the proximal portion 44a of the cam slots 44. Because the first and second cam members 30, 32 move downwardly within the cam slots 44 at the same angle during movement of the first jaw 20 from the intermediate position (FIG. 6) to the clamped position (FIG. 7), the longitudinal axis of the first jaws 20 remains substantially parallel to the second jaw 22 to cause parallel closure of the first and second jaws 20, 22. This allows even compression of tissue clamped between the first and the second jaws 20, 22 during movement of the first jaw to the clamped position.

Although the description of the operation of the clamping device 10 describes the actuator knob 14a as being moved proximally to move the first and the second jaws 20, 22 from the open position of FIG. 4 to the clamped position of FIG. 7, it is envisioned that the actuator assembly 14 including the actuator knob 14a (FIG. 1) can be biased to urge the first and second jaws 20, 22 to the clamped position (FIG. 7) through the use of a biasing member supported within the hand grip 12 or elongate body 16. In such an embodiment, the actuator knob 14a (FIG. 1) would be automatically retracted to move the first and second jaws 20, 22 to the clamped position by the biasing member (not shown) but would have to be advanced in relation to the hand grip 12 to move the first and second jaws 20, 22 to the open position (FIG. 4).

FIGS. 8-12 illustrate an alternate embodiment of the tool assembly of the presently disclosed surgical clamping device shown generally as tool assembly 118. The tool assembly 118 is similar to the tool assembly 18 and includes a first jaw 120 and a second jaw 122. In contrast to the tool assembly 18, the first jaw 120 of the tool assembly 118 includes a proximal portion 134 having first and second side walls 138, 140 that define a cavity 142, and first and second cam members 130, 132 that extend across the cavity 142, and the second jaw 132 includes a central body portion 128 that defines a cam slot 144. The central body portion 128 of the second jaw 122 is received within the cavity 142 of the first jaw 120 such that the first and second cam members 130, 132 are received within the cam slot 144. The cam slot 144 has a shape that is substantially the same as the shape of the cam slots 44 described above in regard to the tool assembly 18. More specifically, the cam slot 144 has a proximal portion 144a that defines an acute "Ω" and a distal portion 144b that defines an acute angle "ß" wherein the acute angle "ß" defined by the distal portion 144b of the cam slot 144 is greater than the angle "Ω" defined by the proximal portion 144a of the cam slot 144.

Figure 10:
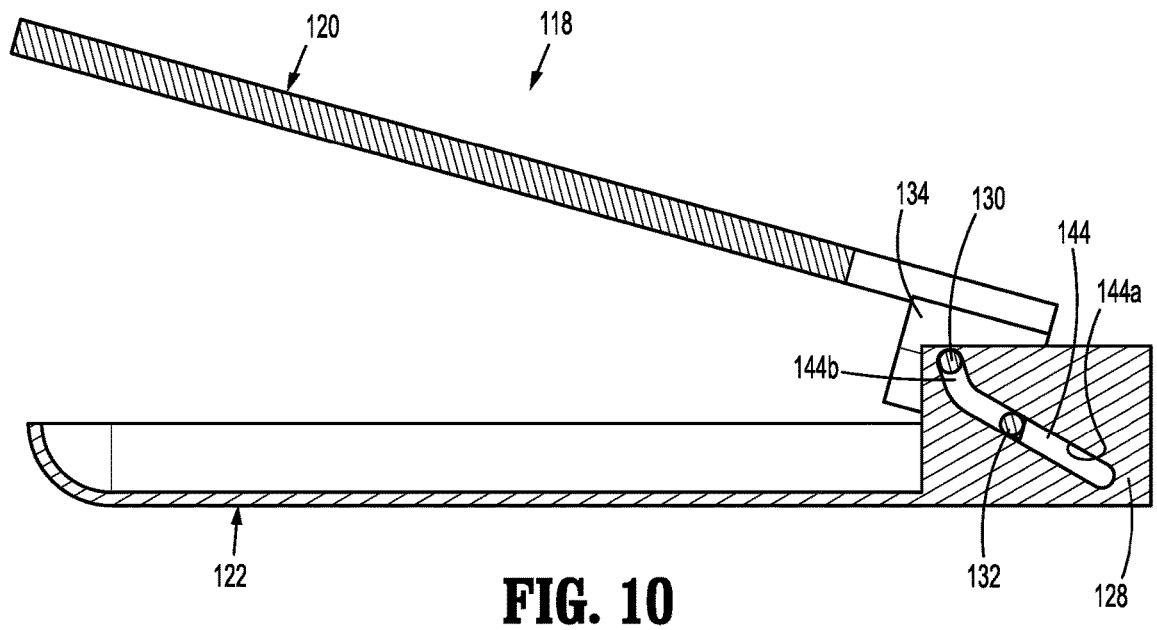
FIG. 10 is a cross-sectional view taken along section line 10-10 of FIG. 8.

Referring to FIG. 10, when the first jaw 120 is in its advanced position in relation to the second jaw 122, the first cam member 130 is positioned in the distal portion 144b of the cam slot 144 and the second cam member 132 is positioned in the proximal portion 144a of the cam slot 44. In this position, the first jaw 120 is in the open position to facilitate placement of tissue between the first and second jaws 120, 122.

Figure 11:
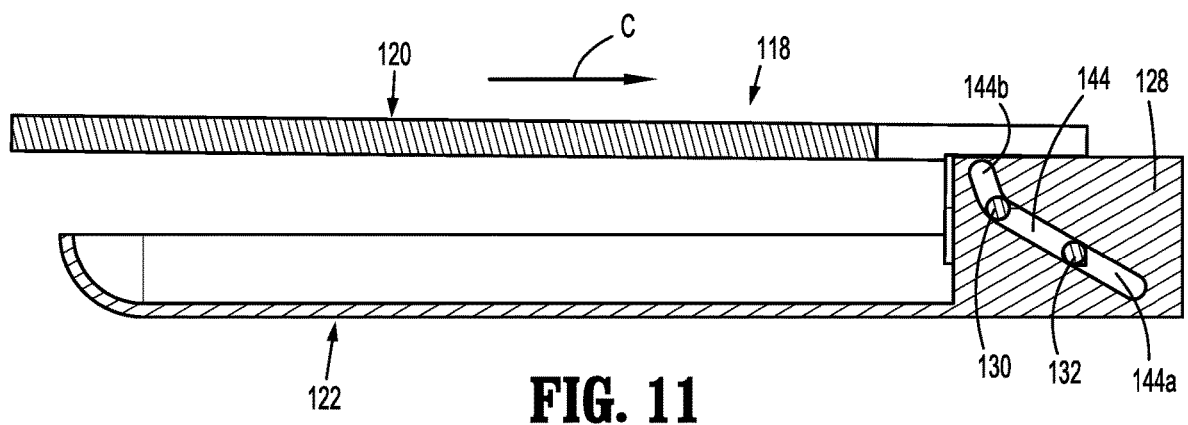
FIG. 11 is a side view of the tool assembly shown in FIG. 10 with the jaws in the intermediate position.

Referring to FIG. 11, when the actuator knob 14a (FIG. 1) of the actuator assembly 14 is retracted to move the first jaw 120 proximally in relation to the second jaw 122 in the direction indicated by arrow "C", the first and second cam members 130, 132 are moved proximally within the cam slot 144 of the second jaw 122 such that the first cam member 130 moves from the distal portion 144b of the cam slot 144 to the proximal portion 144a of the cam slot 44. As the cam member 130 moves through the distal portion 144b of the cam slot 144 at the angle "ß" and the second cam member 132 moves through the proximal portion 144a of the cam slot 44 at an angle "Ω", the first jaw 120 rotates in relation to the second jaw 22 from the open position to an intermediate position. In the intermediate position, the first jaw 120 defines a longitudinal axis that is substantially parallel to a longitudinal axis of the second jaw 122.

Figure 12:
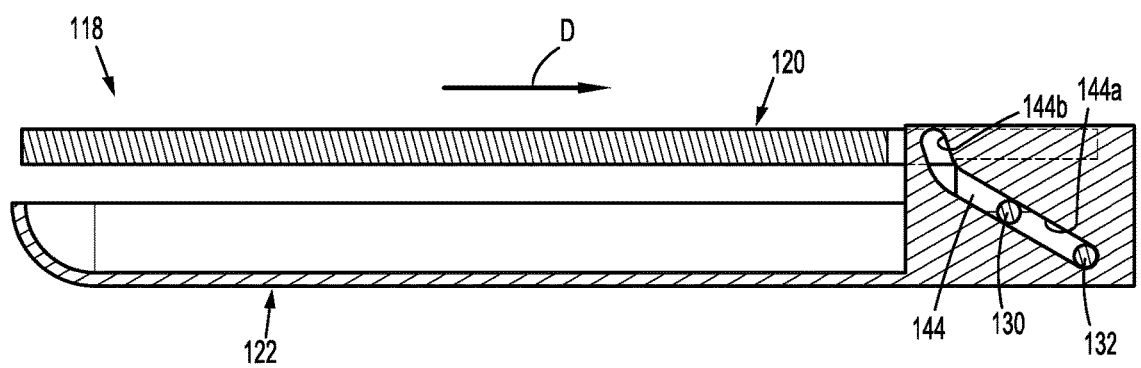
FIG. 12 is a side view of the tool assembly shown in FIG. 10 with the jaws in the clamped position.

Referring to FIG. 12, when the actuator knob 14a (FIG. 1) is retracted to move the first jaw 120 in relation to the second jaw 122 in the direction indicated by arrow "D" to a fully retracted position, the first and second cam members 130, 132 move downwardly along the proximal portion 144a of the cam slot 144. Because the first and second cam members 130, 132 move downwardly within the cam slots 144 at the same angle during movement of the first jaw 120 in relation to the second jaw 122 from the intermediate position (FIG. 11) to the clamped position (FIG. 12), the longitudinal axis of the first jaws 120 remains substantially parallel to the second jaw 122 to cause parallel closure of the first and second jaws 120, 122. This allows for even compression of tissue as the tissue is clamped between the first and the second jaws 120, 122.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical clamping device comprising:
 a hand grip;
 an actuator assembly supported on the hand grip;
 an elongate body defining a longitudinal axis and extending from the hand grip;
 a tool assembly supported on the elongate body, the tool assembly having a first jaw including a mount portion and a clamping portion, and a second jaw including a proximal portion having first and second side walls defining a central cavity, the mount portion of the first jaw being received within the central cavity of the second jaw, one of the mount portion of the first jaw or the proximal portion of the second jaw including first and second cam members and the other of the mount portion of the first jaw or the proximal portion of the second jaw defining at least one cam slot, the first and second cam members being received in the at least one cam slot, the at least one cam slot including a distal portion defining an acute angle "ß" with the longitudinal axis and a proximal portion defining a second acute angle "Ω" with the longitudinal axis, wherein the angle "ß" is greater than the angle "Ω".

2. The surgical clamping device of claim 1, wherein the mount portion of the first jaw includes the first and second cam members and the proximal portion of the second jaw defines the at least one cam slot.

3. The surgical clamping device of claim 2, wherein each of the first and second walls of the proximal portion of the second jaw defines a cam slot of the at least one cam slot.

4. The surgical clamping device of claim 3, wherein the first and second cam members are longitudinally spaced from each other on the mount portion of the first jaw.

5. The surgical clamping device of claim 4, wherein the first and second cam members extend radially outwardly from opposite sides of the mount portion of the first jaw.

6. The surgical clamping device of claim 1, wherein the mount portion of the first jaw defines the at least one cam slot.

7. The surgical clamping device of claim 6, wherein the proximal portion of the second jaw supports the first and second cam members.

8. The surgical clamping device of claim 7, wherein the first and second cam members extend between the first and second side walls of the proximal portion of the second jaw across the central cavity.

9. The surgical clamping device of claim 1, wherein the first and second cam members are longitudinally spaced from each other.

10. A tool assembly comprising:
 a first jaw including a mount portion and a clamping portion; and
 a second jaw including a proximal portion having first and second side walls defining a central cavity, the mount portion of the first jaw being received within the central cavity of the second jaw;
 wherein one of the mount portion of the first jaw or the proximal portion of the second jaw includes first and second cam members and the other of the mount portion of the first jaw or the proximal portion of the second jaw defines at least one cam slot, the first and second cam members being received in the at least one cam slot, the at least one cam slot including a distal portion defining an acute angle "ß" with a longitudinal axis of the tool assembly and a proximal portion defining a second acute angle "Ω" with the longitudinal axis of the tool assembly, wherein the angle "ß" is greater than the angle "Ω".

11. The tool assembly of claim 10, wherein the mount portion of the first jaw includes the first and second cam members and the proximal portion of the second jaw defines the at least one cam slot.

12. The tool assembly of claim 11, wherein each of the first and second walls of the proximal portion of the second jaw defines a cam slot of the at least one cam slot.

13. The tool assembly of claim 12, wherein the first and second cam members are longitudinally spaced from each other on the mount portion of the first jaw.

14. The tool assembly of claim 13, wherein the first and second cam members extend radially outwardly from opposite sides of the mount portion of the first jaw.

15. The tool assembly of claim 10, wherein the mount portion of the first jaw defines the at least one cam slot.

16. The tool assembly of claim 15, wherein the proximal portion of the second jaw supports the first and second cam members.

17. The tool assembly of claim 16, wherein the first and second cam members extend between the first and second side walls of the proximal portion of the second jaw across the central cavity.

18. The tool assembly of claim 10, wherein the first and second cam members are longitudinally spaced from each other.

* * * * *